US012648806B2

(12) United States Patent
Carlson et al.

(10) Patent No.: US 12,648,806 B2
(45) Date of Patent: Jun. 9, 2026

(54) MEDICAL SYSTEMS, DEVICES, AND RELATED METHODS THEREOF

(71) Applicant: Boston Scientific Scimed, Inc., Maple Grove, MN (US)

(72) Inventors: Steven T. Carlson, St. Paul, MN (US); Jeremy Jevne, Ham Lake, MN (US); Scott Jevne, St Anthony, MN (US); Blake Bolthouse, Grand Rapids, MI (US); Niraj Prasad Rauniyar, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 798 days.

(21) Appl. No.: 17/806,115

(22) Filed: Jun. 9, 2022

(65) Prior Publication Data

US 2022/0395320 A1     Dec. 15, 2022

Related U.S. Application Data

(60) Provisional application No. 63/209,087, filed on Jun. 10, 2021.

(51) Int. Cl.
| *A61B 18/14* | (2006.01) |
| *A61B 18/00* | (2006.01) |
| *A61B 18/04* | (2006.01) |

(52) U.S. Cl.
CPC .............................. *A61B 18/1477* (2013.01); *A61B 2018/00577* (2013.01); *A61B 2018/00744* (2013.01); *A61B 2018/00922* (2013.01); *A61B 2018/048* (2013.01)

(58) Field of Classification Search
None
See application file for complete search history.

(56) References Cited

U.S. PATENT DOCUMENTS

| 2008/0161804 A1* | 7/2008 | Rioux ................ A61B 18/1477 606/41 |
| 2009/0216220 A1* | 8/2009 | Hoey ................... A61B 18/082 606/27 |
| 2011/0118815 A1* | 5/2011 | Kuzma .................... A61N 1/05 607/116 |
| 2011/0238144 A1 | 9/2011 | Hoey et al. |
| 2011/0282344 A1* | 11/2011 | Whayne ............. A61B 18/1492 606/49 |

(Continued)

FOREIGN PATENT DOCUMENTS

| JP | H0345232 A | 2/1991 |
| JP | 2009066252 A | 4/2009 |

(Continued)

*Primary Examiner* — Ankit D Tejani
(74) *Attorney, Agent, or Firm* — Bookoff McAndrews, PLLC

(57) ABSTRACT

A medical device may comprise a handle having at least one actuator, a shaft having a proximal end, a distal end, and a lumen extending therebetween, the proximal end connected to the handle, the shaft including a distal articulable section including a distal tip, wherein the distal articulable section is configured to be articulated along a plane, a needle having a delivery lumen, the needle being movably positioned within the lumen of the shaft, and a vapor generator in fluid communication with the delivery lumen.

20 Claims, 5 Drawing Sheets

(56)     References Cited

U.S. PATENT DOCUMENTS

| 2013/0150673 | A1 |     | 6/2013 | Kakehashi |
| 2013/0253505 | A1 |     | 9/2013 | Schultz et al. |
| 2014/0074081 | A1 |     | 3/2014 | Burnett et al. |
| 2016/0287264 | A1 |     | 10/2016 | Chegini et al. |
| 2017/0074081 | A1 |     | 3/2017 | Torrey et al. |
| 2017/0326337 | A1 | * | 11/2017 | Romoscanu ........... A61B 34/30 |
| 2018/0168711 | A1 | * | 6/2018 | Hoey ..................... A61B 18/04 |
| 2021/0059749 | A1 | * | 3/2021 | Sharma ............. A61B 18/1492 |
| 2021/0085390 | A1 |     | 3/2021 | Kadamus et al. |
| 2021/0162174 | A1 |     | 6/2021 | Diolaiti |

FOREIGN PATENT DOCUMENTS

| JP | 2013523220 | A | 6/2013 |
| JP | 2013208429 | A | 10/2013 |
| JP | 2014236788 | A | 12/2014 |
| JP | 2017509410 | A | 4/2017 |
| JP | 2018510026 | A | 4/2018 |
| JP | 2020501746 | A | 1/2020 |
| WO | 2012161021 | A1 | 11/2012 |

* cited by examiner

MEDICAL SYSTEMS, DEVICES, AND RELATED METHODS THEREOF

CROSS-REFERENCE TO RELATED APPLICATION(S)

This patent application claims the benefit of priority under 35 U.S.C. § 119 to U.S. Provisional Patent Application No. 63/209,087, filed Jun. 10, 2021, which is herein incorporated by reference in its entirety.

TECHNICAL FIELD

Various aspects of the present disclosure relate generally to medical systems, devices, and related methods. More specifically, the present disclosure relates to medical systems, devices, and methods for delivering vapor to tissue in a medical procedure.

BACKGROUND

Certain medical conditions, such as conditions of the prostate, may be treated by ablation, including by vapor ablation. Such ablation may be performed using a device having a shaft that is inserted into a body lumen or otherwise into a body of a patient. Vapor (e.g., water vapor) may be released from the device in order to ablate tissue, such as prostate tissue, or to otherwise treat tissue. Current devices may include a flexible vapor delivery tube contained within a rigid sheath, which may result in patient discomfort, challenges in delivering the device to a target location, and potential inadvertent perforation of patient anatomy.

The systems, devices, and methods of the current disclosure may rectify some of the deficiencies described above, and/or address other aspects of the prior art.

SUMMARY

Aspects of the disclosure relate to, among other things, medical systems, devices, and methods of vapor delivery. Each of the examples disclosed herein may include one or more of the features described in connection with any of the other disclosed examples.

According to certain aspects of the disclosure, a medical device comprising a handle having at least one actuator, a shaft having a proximal end, a distal end, and a lumen extending therebetween, the proximal end connected to the handle, the shaft including a distal articulable section including a distal tip, wherein the distal articulable section is configured to be articulated along a plane, a needle having a delivery lumen, the needle being movably positioned within the lumen of the shaft, and a vapor generator in fluid communication with the delivery lumen.

The at least one actuator of the medical device may include a first actuator configured to articulate the distal articulable section in at least a first direction along the plane. The first actuator may be further configured to articulate the distal articulable section in a second direction, opposite the first direction. The medical device may include a cam configured for movement with the at least one actuator; and a first member coupled to the cam such that, upon rotation of the at least one actuator in a first rotational direction, the first member is tensioned thereby articulating the distal articulable section along the plane in a first direction. The medical device may further include a second member coupled to the cam such that, upon rotation of the at least one actuator in a second rotational direction opposite the first rotational direction, the second member is tensioned thereby articulating the distal articulable section along the plane in a second direction opposite the first direction. The medical device may further include a plurality of slots extending along a length of the distal articulable section; and at least two longitudinally extending control members, wherein simultaneous tensioning of the at least two longitudinally extending control members reduces space between the plurality of slots and stiffens of the shaft. The medical device may further include a second actuator, wherein actuation of the second actuator drives the needle from a delivery configuration in which a distal tip of the needle is housed within the shaft, and a treatment configuration in which the distal tip of the needle extends radially outwardly from the shaft. The shaft of the medical device may include a shaft body and a liner surrounding the shaft body. Further, the liner may include a plurality of slots.

Additionally, the distal articulable section of the medical device may be configured to be articulated along the plane in a first direction and prevented from articulating along the plane in a second direction opposite the first direction. The distal articulable section may also include a plurality of alternating slots on at least two sides of the shaft.

The shaft of the medical device may include at least one aspiration or irrigation lumen, and at least one channel for receipt of a wire bundle. The shaft may further include at least one additional lumen, the at least one additional lumen configured for receipt of at least one longitudinally extending member having a distal end configured for articulation of the distal articulable section. The shaft may also include at least two additional lumens, each of the at least two additional lumens configured for receipt of a longitudinally extending member having a distal end configured for articulation of the distal articulable section. Further, the lumen of the shaft may define a plurality of radially inwardly extending protrusions.

According to another aspect of the disclosure, the medical device may comprise a handle having a first actuator and a second actuator; a shaft having a proximal end, a distal end, and a needle lumen extending therebetween, the shaft including: a distal articulable section configured to be articulated along a plane upon actuation of the first actuator; a needle having a delivery lumen, the needle being movably positioned within the needle lumen, and movable between a delivery configuration in which a distal tip of the needle is housed within the needle lumen, and a treatment configuration in which the distal tip of the needle extends radially outwardly from the shaft; and a vapor generator in fluid communication with the delivery lumen. The handle may further include a cam configured for movement with the first actuator, and a first member coupled to the cam such that, upon rotation of the first actuator in a first rotational direction, the first member is tensioned thereby articulating the distal articulable section along the plane in a first direction. The medical device may include a second member coupled to the cam such that, upon rotation of the first actuator in a second rotational direction opposite the first rotational direction, the second member is tensioned thereby articulating the distal articulable section along the plane in a second direction opposite the first direction.

Another aspect of this disclosure may include a method of delivering vapor ablation therapy. The method may include advancing a shaft of a medical device to a location within a body of a subject while the shaft is in a first, relatively flexible configuration, actuating a first actuator of the medical device so as to transition the shaft of the medical device to a second, relatively stiffened configuration, actuating a second actuator of the medical device to drive a needle positioned within a needle lumen of the shaft from a delivery configuration in which a distal tip of the needle is housed within the needle lumen, and a treatment configuration in which the distal tip of the needle extends radially outwardly from the shaft, and delivering vapor treatment to a tissue of the body of the subject via a delivery lumen of the needle. The method may further include articulating the shaft in a first direction along a plane while preventing articulation of the shaft in a second direction opposite the first direction along the plane.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate examples of the present disclosure and together with the description, serve to explain the principles of the disclosure.

DETAILED DESCRIPTION

As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." As used herein, the term "proximal" means a direction closer to an operator and the term "distal" means a direction further from an operator.

Examples of the disclosure may relate to devices and methods for performing various medical procedures and/or treating portions of the large intestine (colon), small intestine, cecum, esophagus, any other portion of the gastrointestinal tract, and/or any other suitable patient anatomy (collectively referred to herein as a "target treatment site"). Various examples described herein include single-use or disposable medical devices. Any structures of the medical devices described herein can be made of biocompatible materials, including biocompatible polymers, rubbers, plastics, and the like.

Aspects of the disclosure relate to, among other things, the delivery of vapor through a flexible shaft of a medical device, such as a vapor ablation device. In embodiments, the medical systems, devices, and methods of the present disclosure may be used to treat a patient's prostate, for example, to treat benign prostatic hyperplasia ("BPH"), or prostate gland enlargement, which can lead to uncomfortable urinary symptoms, blockages of the flow of urine from the bladder, along with other bladder, urinary tract, or kidney issues.

The medical device may be introduced into a body of a patient via a cavity of a body lumen, for example the urethra, via a natural orifice. Delivery and placement of the medical device can also be in other body lumens or organs reachable via a natural orifice, body tract, or bodily incision. Once in position, a vapor generator, contained within or in communication with the medical device, may be activated to generate water vapor. The water vapor may be conveyed to a treatment site (e.g., via a needle) in order to therapeutically treat a tissue. For example, the vapor may ablate the tissue. In one example, the ablated tissue may be prostate tissue, and the ablation may treat benign prostatic hyperplasia (BPH). Although vapor ablation is referenced herein, such references should not be construed as limiting. The examples disclosed herein may also be used with other types of ablation mechanisms (e.g., cryoablation, RF ablation, or other types of ablation) or with other devices not relating to ablation.

Reference will now be made in detail to examples of the present disclosure described above and illustrated in the accompanying drawings. Wherever possible, the same reference numbers will be used throughout the drawings to refer to the same or like parts.

Figure 1:
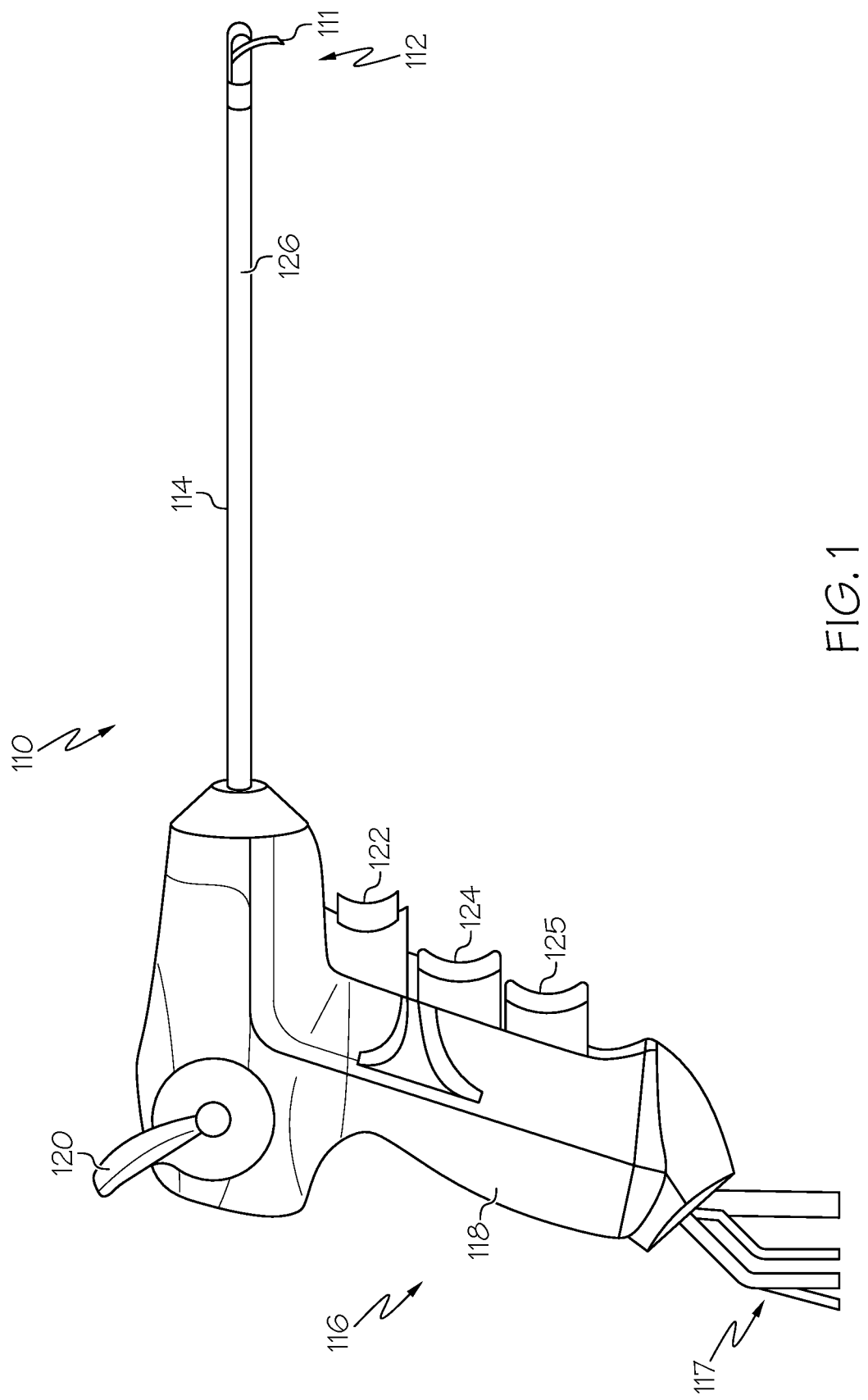
FIG. 1 is a side view of a medical device, according to aspects of this disclosure.

FIG. 1 shows a side view of an exemplary ablation device 110. Ablation device 110 may include a handle assembly 116 and a shaft 114. Shaft 114 may be insertable into a body lumen of a patient or otherwise into a body of a patient (e.g., through a tissue of a patient, such as via a transperineal route). A proximal end of shaft 114 may be connected to handle assembly 116. Shaft 114 may have a distal tip 112. As will be described in further detail herein, shaft 114 may include an actively or passively deflectable (e.g., flexible) shaft (e.g., a coiled shaft) having one or more liners (e.g., a braided tubing, or covering). Handle assembly 116 may be configured to be gripped by a user.

A needle 111 may be extendable and/or retractable from distal tip 112. For example, needle 111 may be movably positioned within a lumen of shaft 114. Needle 111 may be a member having a central lumen or channel extending from a proximal end of needle 111 toward a distal tip of needle 111 (i.e., the central lumen or channel extends between the proximal end of needle 111 and the distal end of needle 111), and a plurality of apertures near the distal tip of needle 111. The plurality of apertures may be configured to communicate the contents of the central lumen or channel (e.g., vapor, steam) to surrounding tissue into which needle 111 is positioned, received, or otherwise inserted. For example, the central lumen or channel of needle 111 (i.e., a delivery lumen of needle 111) may be configured to receive vapor therein (e.g., via a vapor generator) and to deliver the vapor to tissue via the apertures. Needle 111 may be configured to have a first, delivery/insertion configuration, in which needle 111 is contained, received, or otherwise positioned within shaft 114 (e.g., such that no portion of needle 111 extends radially outwardly of distal tip 112, relative to a longitudinal axis of distal tip 112). Needle 111 may have a second, treatment configuration (FIG. 1), in which needle 111 is extended out of distal tip 112 (e.g., distally past and/or radially outwardly of distal tip 112, relative to the longitudinal axis of distal tip 112). Needle 111 may be movably positioned within a lumen of shaft 114 so that it may transition between the delivery configuration and the treatment configuration. In the treatment configuration, needle 111 may curve radially outward relative to the longitudinal axis of shaft 114. Movement of needle 111 between the first, insertion configuration and the second, treatment configuration, and vice versa, may be caused by any mechanical, pneumatic, or magnetic actuation assembly without departing from the scope of this disclosure.

Handle assembly 116 may include cabling 117 extending proximally from a proximal end of handle assembly 116. Cabling 117 may transmit power, fluids, signals, etc. to handle assembly 116 or other portions of ablation device 110 (e.g., shaft 114). In an example, cabling 117 may transmit fluid, such as water, from a fluid source to ablation device 110. In some embodiments, a vapor generator may be disposed within ablation device 110 (e.g., in handle assembly 116 or shaft 114). Fluid to be passed through the vapor generator may be housed within ablation device 110 or may be transmitted to ablation device 110 via cabling 117. In other embodiments, the vapor generator may be disposed externally to ablation device 110, and vapor may be transmitted from the vapor generator to ablation device 110 via cabling 117.

Handle assembly 116 may be configured to be gripped by a user via handle body 118. Handle assembly 116 may include one or more actuators 122, 124, 125 to control various functions of the device. For example, actuator 122 may control the delivery of vapor through the handle assembly 116 and shaft 114 (e.g., may drive needle 111 from a delivery configuration in which a distal tip of needle 111 is housed within shaft 114, and a treatment configuration in which a distal tip of needle 111 extends outwardly (e.g., radially outwardly) from shaft 114), actuator 124 may control the delivery of fluids through the handle assembly 116 and shaft 114, and actuator 125 may control a camera or optics, or any combination thereof. Handle assembly 116 may also include an actuator 120 configured to control the articulation or deflection of the distal tip 112 of shaft 114 (including distal articulable section 126), as will be described further herein. Actuator 120 may be a knob, trigger, button, or any other actuator known in the art. Actuator 120 may be located on a side face of handle assembly 116, e.g., on the left side or right side of the handle body 118 when ablation device 110 is in use.

Shaft 114 may be coupled to the distal end of handle assembly 116. Shaft 114 of ablation device 110 may be a tube having sufficient length to access sites within the body. Additionally, shaft 114 may have sufficient flexibility to traverse tortuous anatomy. Shaft 114 may be insertable into a body lumen of a patient or otherwise into a body of a patient (e.g., through a tissue of a patient, such as via a transperineal route). Distal tip 112 is at or adjacent to the distal end of shaft 114. Distal tip 112 includes a distal articulable or otherwise deflectable section 126 of shaft 114 (e.g., an articulation joint) as will be described in further detail herein. Distal articulation section 126 may include a coiled or otherwise flexible portion of shaft 114 configured for active or passive deflection. As noted above, needle 111 may be extendable and/or retractable from distal tip 112 to deliver treatment (e.g., vapor) to a target tissue site (e.g., prostrate). As mentioned above, and as will be described in further detail below, one or more handle actuators (e.g., actuator 120) and related mechanisms can control the articulation or deflection of distal articulable section 126.

Figure 2:
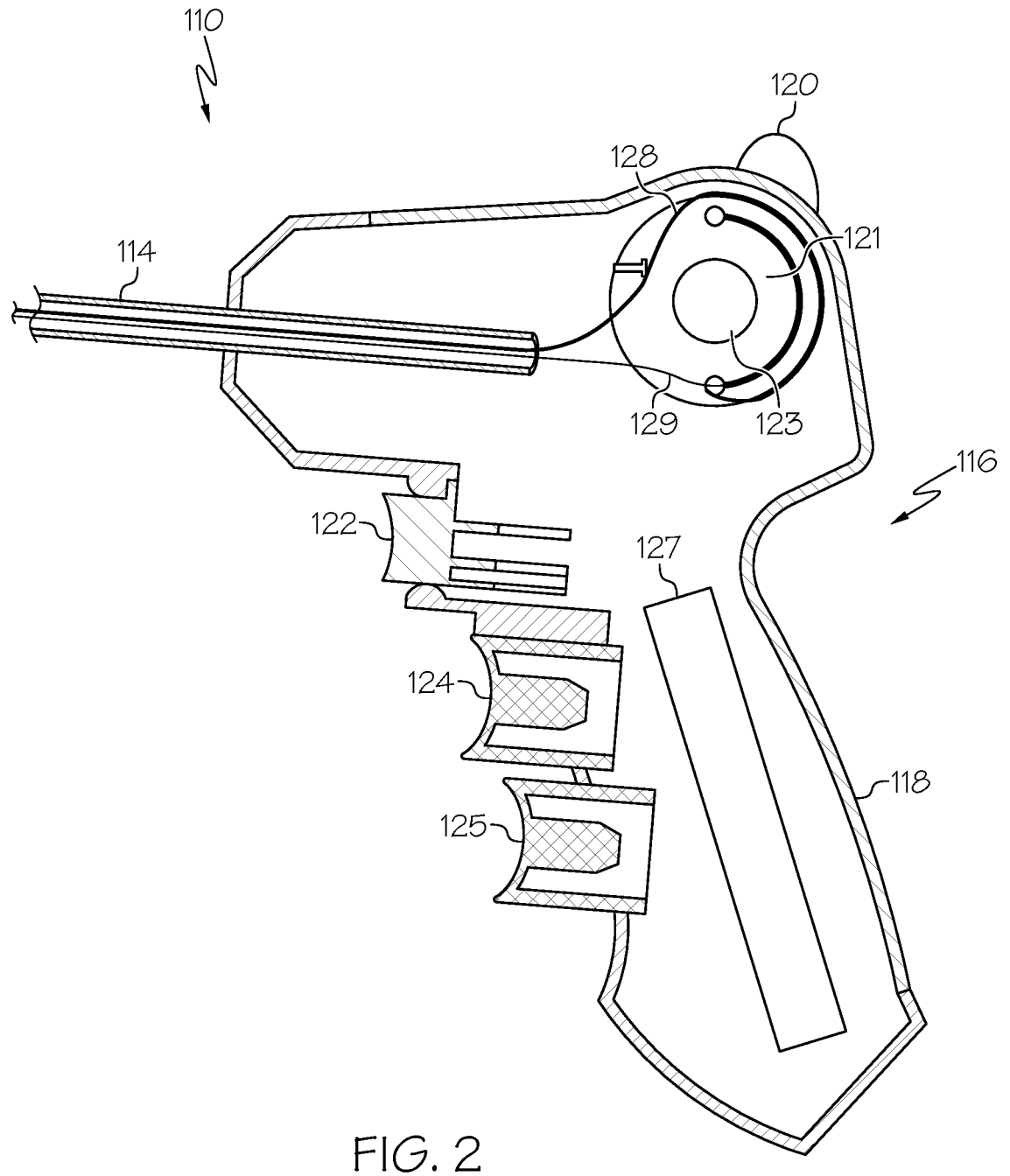
FIG. 2 is a side cross-sectional view of a handle of the medical device of FIG. 1, according to aspects of this disclosure.

FIG. 2 is a side cross-sectional view of the handle assembly 116, showing select components positioned inside of handle body 118 of ablation device 110. It is understood that additional components that may be positioned within handle body 118 have been omitted for clarity. As schematically shown, and as described above, handle body 118 may include a vapor generator 127. Vapor generator 127 may be in fluid communication with needle 111 (e.g., a delivery lumen of needle 111) so as to deliver vapor to tissue. In other arrangements, vapor generator 127 may be located within or along shaft 114 or external to ablation device 110 without departing from the scope of this disclosure. As shown in FIG. 2, a cam 121 is fixedly coupled to actuator 120 by various means known in the art, including, but not limited to, adhesives, ultrasonic welding, etc., or otherwise formed as a one-piece structure such that movement (e.g., rotation) of actuator 120 results in likewise movement (e.g., rotation) of cam 121. For example, cam 121 may be mounted on a pivot 123 about which cam 121 may rotate. Cam 121 may have one or more grooves or channels within which (or along which) one or more longitudinally extending members 128, 129 may be positioned. A proximal end of each of longitudinally extending members 128, 129 may be coupled to cam 121 by various means known in the art, including, but not limited to, adhesives, ultrasonic welding, etc. Longitudinally extending members 128, 129 extend through shaft 114 toward the distal end thereof (not shown). A distal end of longitudinally extending member 128, 129 may be coupled via any appropriate means to a portion of shaft 114 (e.g., distal articulable section 126) such that tensioning or relaxing one or more of longitudinally extending members 128, 129 may result in articulation or deflection of distal articulable section 126. For example, as actuator 120 is rotated in a first rotational direction (e.g., clockwise), a tension force is imparted to longitudinally extending member 128 thereby resulting in distal articulable section 126 articulating in a first direction along a plane (e.g., in an upward direction). Further, as actuator 120 is rotated in a second rotational direction (e.g., counter-clockwise), a tension force is imparted to longitudinally extending member 129 thereby resulting in distal articulable section 126 articulating in a second direction along the plane (e.g., in a downward direction). It is understood that in some arrangements, only a single (e.g., only one) longitudinally extending member may be utilized. For example, ablation device 110 may include longitudinally extending member 128 but omit longitudinally extending member 129. In such an arrangement, distal articulable section 126 may be biased (e.g., naturally or otherwise biased) toward a neutral (e.g., straight) configuration (such as that depicted in FIG. 1). Further, in such an arrangements, as actuator 120 is rotated in a first rotational direction (e.g., clockwise), a tension force is imparted to longitudinally extending member 128 thereby resulting in distal articulable section 126 articulating in a first direction along a plane (e.g., in an upward direction). Further, as actuator 120 is rotated in a second rotational direction (e.g., counter-clockwise) longitudinally extending member 128 may relax, thereby resulting in distal articulable section 126 returning to the neutral (e.g., straight, undeflected) configuration. In such a case, rotation of shaft 114 may be required to orient needle 111 and shaft 114 in an alternative direction or orientation. Further, it is understood that while up/down articulation is described herein, ablation device 110 can also be articulated left or right in similar fashion, depending on the attachment position of the longitudinally extending member(s) 128, 129 to the distal end of shaft 114 (e.g., distal articulable section 126).

Figure 3A:
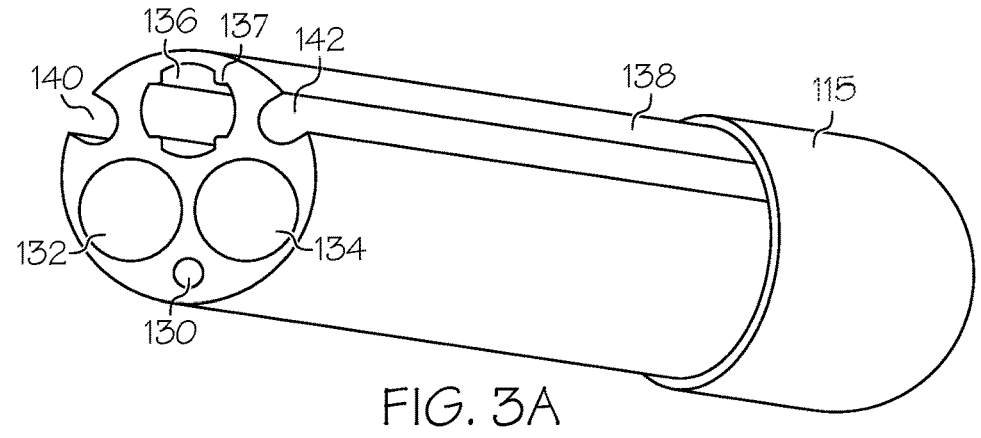
FIGS. 3A-3C depict exemplary cross-sectional views of shafts of the medical device of FIG. 1, according to aspects of this disclosure.
Figure 3B:
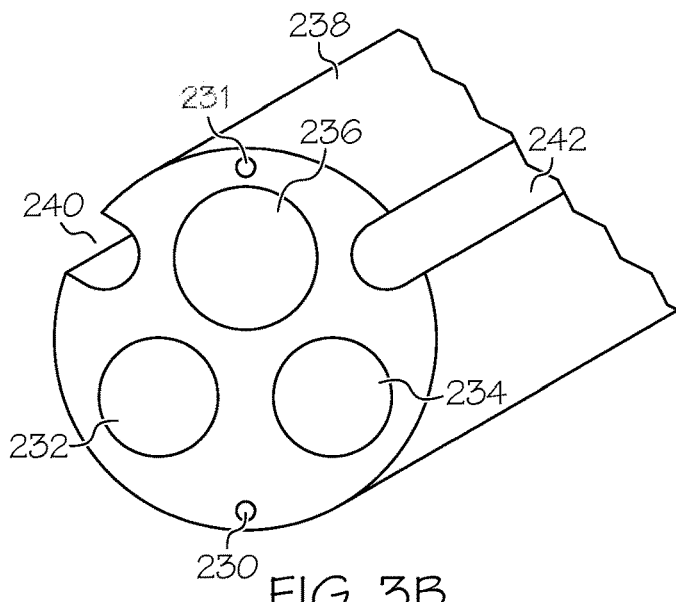
Figure 3C:
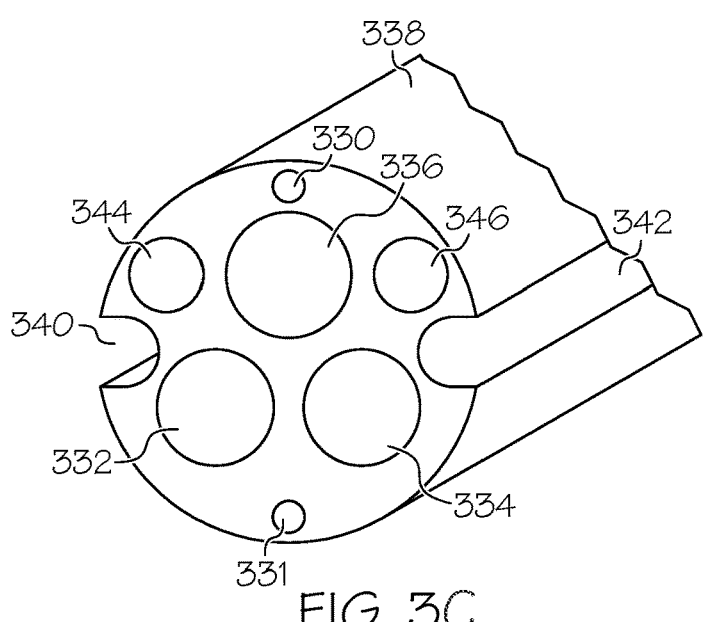

FIGS. 3A-C depict cross-sectional views of various embodiments of shaft 114. As shown in FIG. 3A, for example, shaft 114 may include shaft body 138 and a sheath, tube, or liner 115 surrounding an outer surface of shaft body 138. Shaft body 138 may extend from a proximal-most end of shaft 114 to the distal-most end of shaft 114. Shaft body 138 may include a plurality of fully enclosed lumens 132, 134, 136 that extend throughout the entire length of the shaft 114. Lumens 132, 134, 136 are substantially parallel to each other, so that longitudinal axes of lumens 132, 134, 136 are substantially parallel to each other and to a central longitudinal axis of shaft body 138, which extends from the distal-most end of the sheath to the proximal-most end of shaft body 138. Lumens 132, 134, 136 may be open at a distal face of shaft body 138. Lumen 136 may include one or many protrusion(s) 137 extending radially inwardly from the lumen wall. For example, a wall of lumen 136 may define protrusions 137. These protrusions create air gaps between needle 111 (FIG. 1) and the lumen wall of lumen 136. The air gaps created by the one or many protrusion(s) 137 may help reduce heat exchange between the hot vapor needle and the surrounding shaft components. This ensures the vapor maintains its stored energy, and prevents the shaft exteriors from getting excessively hot. Lumens 132, 134 may be interchangeably and/or simultaneously used to provide saline or an irrigation medium to the tissue during a medical procedure. Additionally or alternatively, one or more of lumens 132, 132, 136 may provide aspiration/suction. Shaft body 138 is not limited to contain three lumens 132, 134, 136, as it can contain more or less lumens. Shaft body 138 is connected to handle assembly 116 (shown in FIG. 1) at the proximal end of shaft body 138, thereby permitting access to lumens 132, 134, 136 from the handle assembly 116. The internal walls of lumens 132, 134, 136 may be lined with biocompatible materials, such as expanded polytetrafluoroethylene (ePTFE), to reduce friction for any agent or device being inserted through lumens 132, 134, 136. Further, the cross-sectional shape of fully enclosed lumens 132, 134 may vary in shape. For example, the cross-sectional shape of lumens 132, 134 may be circular, as shown, triangular, square, hexagonal, etc., or any combination thereof. Additionally, any one or more of lumens 132, 134, 136 may have a cross-sectional shape or size different from that of any of other the lumens 132, 134, 136.

Shaft body 138 may further include one or more channels 140, 142. For example, channel 140 may be sized to receive a wire bundle (not pictured). The wire bundle may be comprised of electrical wires needed to facilitate the use of a camera or light emitting diode (LED) located at the distal tip (not shown). Channel 142, for example, may likewise be sized to receive a wire bundle (not pictured). Channels 140, 142 may be lined with biocompatible materials, such as ePTFE, to reduce friction for a wire bundle being inserted along the longitudinal axis of channels 140, 142.

Additionally, shaft body 138 may include a further lumen 130 that is fully enclosed within shaft body 138. A longitudinal axis of lumen 130 extending from the proximal-most end to the distal-most end of shaft body 138 is substantially parallel to each of lumens 132, 134, 136 and the central longitudinal axis of shaft body 138. Lumen 130 may be open at a distal face of shaft body 138. At least one longitudinally extending member 128, 129 (as exemplified in FIG. 2) may extend from the distal end of shaft body 138 to the proximal end of shaft body 138, along the longitudinal axis of lumen 130. Alternatively, the at least one longitudinally extending member 128, 129 may extend from the distal end of the shaft body 138 to a proximal portion of the shaft body. As previously mentioned, one or more of the longitudinally extending members 128, 129 may be coupled to a portion of the distal tip 112 (e.g., distal articulable section 126) in order to enable articulation of the distal end of shaft 114.

The entirety of shaft body 138 may be comprised of materials of sufficient column strength to prevent kinking during articulation. The number of lumens is dependent on, among other things, the cross-sectional area and material of shaft body 138. For example, the material and walls of shaft body 138 may be selected so as to provide sufficient structural support to prevent lumens 132, 134, 136, and/or channels 140, 142 from collapsing.

FIG. 3B shows an alternate embodiment of a cross-section of a shaft body 238. Similar to the previous embodiment, the shaft body 238 is comprised of a plurality of fully enclosed lumens 232, 234 that extend throughout the entire length of shaft body 238. However, lumen 236 may omit the plurality of protrusions 137 exemplified in lumen 136 of FIG. 3A. The lumens 232, 234, 236 may be lined with biocompatible materials, such as expanded polytetrafluoroethylene (ePTFE), to reduce friction for any agent or device being inserted through the lumens. Further, the cross-sectional shape of fully enclosed lumens 232, 234, 236 may vary in shape and/or size. For example, the cross-sectional shape of lumens 232, 234, 236 may be circular, as shown, triangular, square, hexagonal, etc., or any combination thereof. Channels 240, 242 of FIG. 3B may also include the same or similar structures as described in FIG. 3A. In the arrangement of FIG. 3B, shaft body 238 includes lumen 230 and a lumen 231, located on opposing sides from each other in the cross-sectional view of the sheath (e.g., located along diametrically opposed portions of shaft body 238). For example, lumen 231 is in the 12 o'clock position and lumen 230 is in the 6 o'clock position relative to a central longitudinal axis of shaft body 138. At least two longitudinally extending members, 128, 129 (as exemplified in FIG. 2) may extend from the distal end of shaft body 238 to the proximal end of shaft body 238, along the longitudinal axes of lumens 230, 231, respectively. The at least two longitudinally extending members 128, 129 may enable the articulation or deflection of the articulable section 126, shown in FIG. 1. Alternatively, the at least two longitudinally extending members 128, 129 may enable the stiffening or tightening of the articulable section 126, shown in FIG. 1. For example, simultaneously tensioning both longitudinally extending members 128, 129 may result in stiffening of shaft body 238.

FIG. 3C shows an alternate embodiment of a cross-section of a shaft body 338. As shown in FIG. 3C, shaft body 338 may be comprised of a plurality of lumens 332, 334, 336, similar to the arrangement shown in FIG. 3A. Channels 340, 342 may be located along the left and right sides of shaft body 338, respectively. Further, shaft body 338 may include additional lumens 344, 346 for irrigating and cooling the tissue during a medical procedure. Lumens 344, 346 may be located on the left and right sides of lumen 336. Additionally, lumens 344, 346 may be lined with biocompatible materials, such as expanded polytetrafluoroethylene (ePTFE), to reduce friction for any agent or device being inserted through the lumens.

Similar to shaft body 138, the entirety of shaft bodies 238, 338 may be comprised of materials of sufficient column strength to prevent kinking during articulation. The number of lumens may be dependent on, among other things, the cross-sectional area and material of shaft body 138, 238, 338 and the plurality of lumens thereof. For example, the material and walls of the shaft bodies may be selected to provide sufficient structural support to prevent the various lumens (e.g., 132, 134, 136, 232, 234, 236, 332, 334, 336, 344, 346) and/or channels (e.g., 140, 142, 240, 242, 340, 342) from collapsing.

Figures 4A, 4B, 4C:
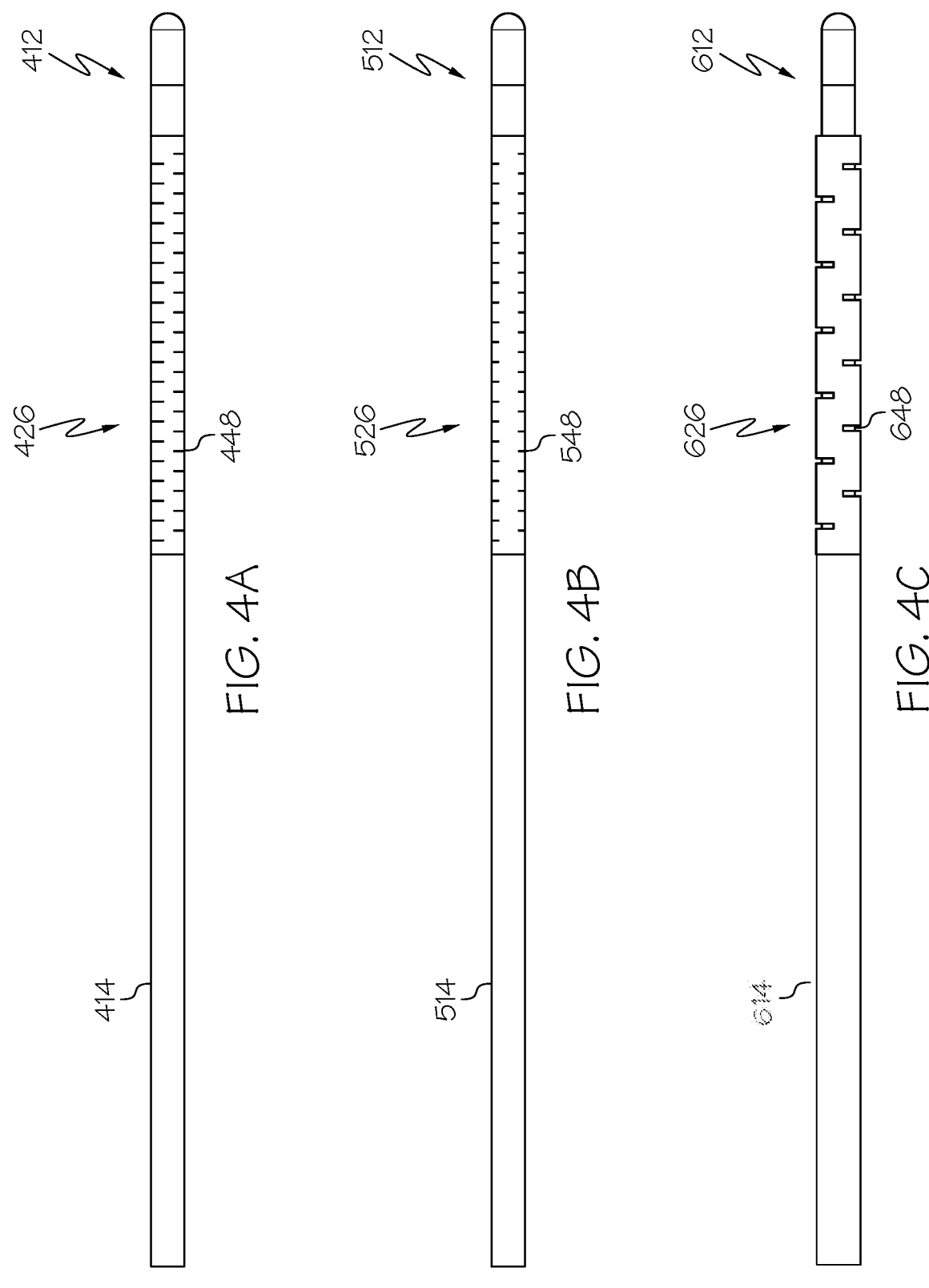
FIGS. 4A-4C depict side views of exemplary distal ends of the shaft of medical device of FIG. 1, according to aspects of this disclosure.

FIGS. 4A-C show various embodiments of a distal portion of a shaft configured for articulation in a single (e.g., only one) plane while maintaining rigidity in other planes. Rigidity is maintained in the plane of needle 111 (FIG. 1) such that an operator can apply necessary force to leverage needle 111 against a treatment site (e.g., a wall of the prostate) during needle 111 deployment. As shown in FIG. 4A, a shaft 414 (similar to shaft 114 of FIG. 1) includes a distal articulable section 426, to be described further herein, and a distal tip 412. In FIG. 4A, the distal end of shaft 414 includes or is otherwise coupled to the proximal-most end of an articulable section 426. The articulable section 426 may include a plurality of slots 448 on opposite sides thereof. The slots 448 may extend perpendicularly or otherwise transverse (e.g., angled) to a central longitudinal axis of articulable section 426. In addition, as shown, the slots 448 may be alternatingly arranged. That is, the slots 448 may be arranged so that a first slot may be on a first side of articulable section 426 and a second slot may be axially positioned between two adjacent slots 448 located on an opposite side of articulable section 426. The slots 448 may extend the entire length or only a portion of the articulable section 426. Although not shown, in some arrangements, slots 448 may extend an entire length or a majority of a length of shaft 414. In some arrangements, slots 448 may extend through an entire wall thickness of articulable section 426, while in other arrangements, the slots 448 may extend through less than an entire wall thickness of articulable section 426, such as, e.g., approximately one-fourth to approximately one-half of the way through the wall thickness of articulable section 426. The plurality of slots 448 may enable the articulation of the distal tip 412 of shaft 414 in at least two directions along a plane. For example, when the distal tip 412 of shaft 414 is articulated up, more space is created between the bottom slots 448 while space between the top slots 448 is reduced. Additionally, when the device is articulated down, space is reduced between the bottom slots while space between the top slots 448 is increased. The alternating configuration of slots 448 may enable the distal articulable section 426 to articulate in at least one plane while maintaining rigidity in at least a second plane to prevent bending the needle 111, exemplified in FIG. 1. As discussed above, simultaneous tensioning of both longitudinally extending members 128, 129 may result in stiffening of shaft body 238 by reducing space between slots 448.

As shown in the further arrangements exemplified by FIGS. 4B-C, slots 548 and 648, respectively, may be of various sizes, lengths, and widths in order to enable various degrees of articulation. Additionally, articulable sections 426, 526, 626 may be made of a same or a different material than a remainder of a respective shaft 414, 514, 614. For example, while the slots 448 of FIG. 4A extend inward approximately one-third of the distance toward a center of articulable section 426, as shown in FIG. 4B, a plurality of slots 548 may extend inward approximately one-fourth of the distance towards the center of articulable section 526. That is, as compared to the slots 448 exemplified in FIG. 4A, the slots 548 of FIG. 4B further limit the articulation of the distal end of shaft 514. FIG. 4C shows an alternate embodiment wherein a width of each of a plurality of alternating slots 648 is increased to enable a smaller bend radius of articulable section 626 during articulation.

Each of the articulable sections 426, 526, 626 shown in FIGS. 4A-C may be controllable via one or more longitudinally extending members 128, 129, as described in connection with FIG. 2. The one or more longitudinally extending members 128, 129 may extend from a respective distal articulable section 426, 526, 626 through at least one of fully enclosed lumens 130, 230, 231, 330, 331 of the embodiments depicted in FIGS. 3A-C, thereby creating an active deflection of a respective distal tip 412, 512, 612. Further, each of the shafts 414, 514, 614 may be made of any one or more materials. For example, a portion of any one of shafts 414, 514, 614 may be comprised of a first material, while a different portion (e.g., distal articulable sections 426, 526, 626) may be comprised of a second material that is different than the first material. Alternatively, the entirety of each of the shafts 414, 514, 614 may be comprised of a single material. Further, any one or more of shafts 414, 514, 614 may include one or more liners (e.g., a braided liner, tubing, or sheath structure) included along at least a portion or an entirety of the respective shaft 414, 514, 614. It is understood that the various materials, quantity of slots, depth of slots, width of slots, arrangement of slots, shaft wall thickness, and any liners may be selected to achieve a desired bending radius or stiffness (e.g., an appropriate bend radius or stiffness conducive to the urethral anatomy).

Figure 5B:
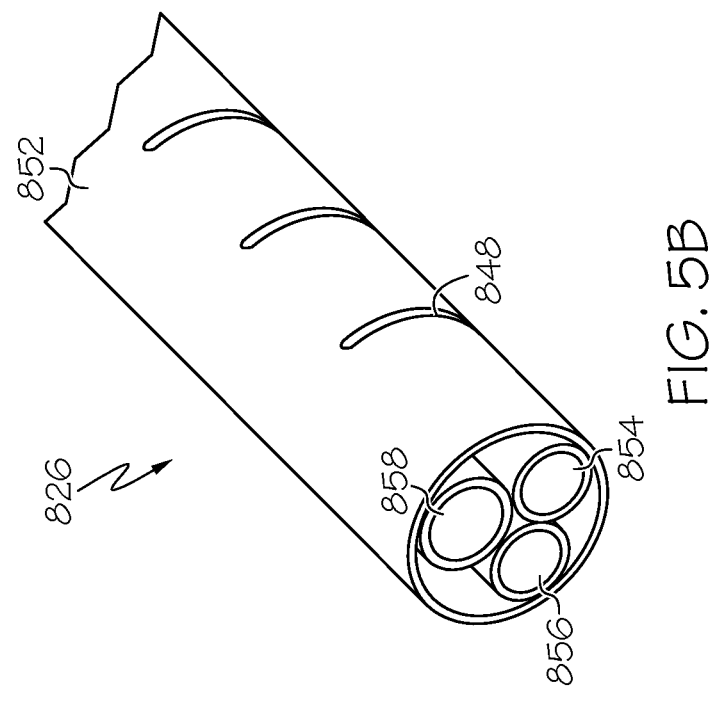
FIGS. 5A-5B depict exemplary cross-sectional views of the distal ends of the shaft of the medical device of FIGS. 4A-4C, according to aspects of this disclosure.
Figure 5A:
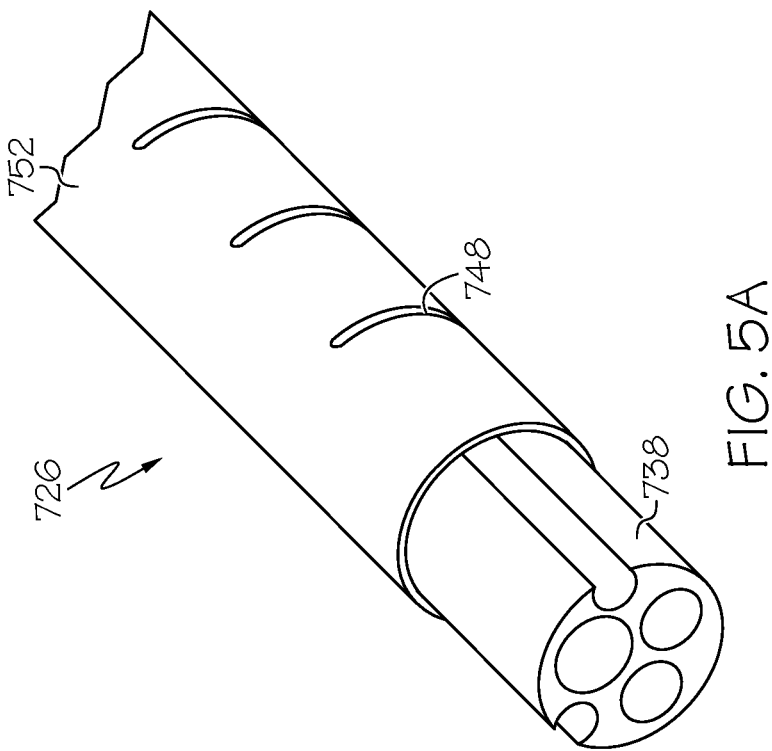

FIGS. 5A and 5B depict exemplary cross-sectional views of alternative embodiments of a distal articulable section 726, 826, respectively. The embodiment depicted in FIG. 5A may include an inner shaft body 738 confined within an articulation tube 752. The articulation tube 752 includes a plurality of slots 748 to enable a passively flexible distal end of shaft 114. In other words, longitudinally extending members may not control the articulation or deflection of the articulable section. Instead, this embodiment may be configured such that a portion of the distal end may bend and flex with a patient's anatomy during a medical procedure.

While the shaft body 738 of FIG. 5A (similar to the shaft bodies 138, 238, 338 illustrated in FIGS. 3A-3C) may be extruded as a one-piece structure, the embodiment depicted in FIG. 5B is comprised of a plurality of separately formed lumens 854, 856, 858 retained within an outer tube 852. In some arrangements, any of the separately formed lumens 854, 856, 858 may be coupled to outer tube 852. This may be accomplished by any means commonly known in the art, such as welding, adhesives, etc. Similar to the embodiment depicted in FIG. 5A, the outer tube 852 includes a plurality of slots 848 to enable a passively flexible distal end. Longitudinally extending members do not control the articulation of the distal articulable section 826. Instead, this embodiment is configured such that a portion of the distal end may bend and flex with a patient's anatomy during a medical procedure.

Aspects of the disclosure include methods of using ablation device 110. To do so, the user may first introduce the distal end of device 110 into the urethra via a natural orifice. Delivery and placement also can be in other body lumens or organs reachable via the urethra, any other natural opening or body tract, bodily incision, or through a delivery device, such as an endoscope or sheath. The user may advance the shaft to a location within the urethra (or other body lumen) to a desired treatment site. Once the desired site is accessed, the user can actuate actuator 120 to control the articulation of the distal end of the medical device in at least one direction. Alternatively, the user may activate actuator 120 to reinforce and/or stiffen at least a portion of the shaft 114 during a medical procedure. This may be accomplished by pulling at least two longitudinally extending members 128, 129 (shown in FIG. 2) along the center axis of shaft 114. Once the desired site is accessed, the user may extend, or actuate, a needle to convey water vapor to a treatment site in order to therapeutically treat a tissue. The systems and methods of the present disclosure may permit flexibility of a shaft needed for delivery of the device to a treatment site, while ensuring a path of steam travelling through the shaft for delivery to the treatment site remains open and unobstructed. That is, the systems and methods of the present disclosure permit flexibility during insertion and positioning, and sufficient strength (e.g., apposition force) to enable effective delivery of steam through the shaft during treatment.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

The invention claimed is:

1. A medical device, comprising:
a handle having an actuator;
a shaft having:
  a shaft body having a proximal end, a distal end, and a lumen extending therebetween, wherein the proximal end is connected to the handle, wherein the shaft body is a one-piece extruded structure, and
  an articulation tube radially surrounding an exterior surface of the shaft body, wherein the articulation tube includes a plurality of slots, wherein the articulation tube is configured to be articulated along a plane;
a needle having a delivery lumen, the needle being movably positioned within the lumen of the shaft body; and
a vapor generator in fluid communication with the delivery lumen,
wherein the shaft body further includes a first channel, wherein a first portion of the first channel is defined by the exterior surface of the shaft body, and wherein a second portion of the first channel is defined by an interior surface of the articulation tube,
wherein the shaft body further includes a second channel, wherein a first portion of the second channel is defined by the exterior surface of the shaft body, and wherein a second portion of the second channel is defined by the interior surface of the articulation tube, and
wherein the lumen is positioned between the first channel and the second channel.

2. The medical device of claim 1,
wherein actuation of the actuator drives the needle from a delivery configuration in which a distal tip of the needle is housed within the shaft body, and a treatment configuration in which the distal tip of the needle extends radially outwardly from the shaft body.

3. The medical device of claim 1, wherein the articulation tube is configured to be articulated along the plane in a first direction and prevented from articulating along the plane in a second direction opposite the first direction.

4. The medical device of claim 1, wherein the articulation tube includes a plurality of alternating slots on at least two sides of the articulation tube.

5. The medical device of claim 1, wherein the lumen of the shaft body is a first lumen, wherein the shaft body further includes:
a second lumen for at least one of aspiration or irrigation; and
a third channel for receipt of an electrical wire.

6. The medical device of claim 5, wherein the first lumen of the shaft body defines a plurality of radially inwardly extending protrusions.

7. The medical device of claim 1, wherein the first channel has a first opening at the exterior surface of the shaft body along a length of the first channel, and
wherein the second channel has an opening at the exterior surface of the shaft along a length of the second channel.

8. A medical device, comprising:
a handle having a first actuator and a second actuator;
a shaft having a proximal end and a distal end, wherein the shaft has a distal articulable section configured to be articulated along a plane upon actuation of the first actuator, and wherein the shaft includes:
  a shaft body defining a needle lumen, a first channel, and a second channel; and
  a sheath radially surrounding an exterior surface of the shaft body,
  wherein a first portion of the first channel is defined by the exterior surface of the shaft body, and wherein a second portion of the first channel is defined by an interior surface of the sheath,
  wherein a first portion of the second channel is defined by the exterior surface of the shaft body, and wherein a second portion of the second channel is defined by the interior surface of the sheath, and
  wherein the needle lumen is positioned between the first channel and the second channel;
a needle having a delivery lumen, the needle being movably positioned within the needle lumen, and movable between a delivery configuration in which a distal tip of the needle is housed within the needle lumen, and a treatment configuration in which the distal tip of the needle extends radially outwardly from the shaft; and
a vapor generator in fluid communication with the delivery lumen.

9. The medical device of claim 8, wherein the shaft is rigid in a plane of the needle, so that, as the needle is transitioned from the delivery configuration to the treatment configuration within a body lumen of a subject, the needle is leveraged against a wall of a treatment site.

10. The medical device of claim 8, wherein the first actuator is configured to articulate the distal articulable section in at least a first direction along the plane.

11. The medical device of claim 10, wherein the first actuator is further configured to articulate the distal articulable section in a second direction, opposite the first direction.

12. The medical device of claim 8, further including:
a cam configured for movement with the first actuator; and
a first member coupled to the cam such that, upon rotation of the first actuator in a first rotational direction, the first member is tensioned, thereby articulating the distal articulable section along the plane in a first direction.

13. The medical device of claim 12, further including:

a second member coupled to the cam such that, upon rotation of the first actuator in a second rotational direction opposite the first rotational direction, the second member is tensioned, thereby articulating the distal articulable section along the plane in a second direction opposite the first direction.

14. The medical device of claim 8, wherein a plurality of slots extend along a length of the distal articulable section, and wherein the medical device further comprises:

at least two longitudinally extending control members, wherein simultaneous tensioning of the at least two longitudinally extending control members reduces a space between the plurality of slots and stiffens of the shaft.

15. The medical device of claim 8, wherein actuation of the second actuator drives the needle from the delivery configuration in which the distal tip of the needle is housed within the shaft, and the treatment configuration in which the distal tip of the needle extends radially outwardly from the shaft.

16. The medical device of claim 15, wherein the sheath includes a plurality of slots.

17. The medical device of claim 8, wherein the distal articulable section is configured to be articulated along the plane in a first direction and prevented from articulating along the plane in a second direction opposite the first direction.

18. The medical device of claim 8, wherein the distal articulable section includes a plurality of alternating slots on at least two sides of the shaft.

19. The medical device of claim 8, further comprising: a wire bundle disposed in the first channel, wherein the distal tip includes a camera, wherein the wire bundle is electrically coupled to the camera.

20. The medical device of claim 8, wherein the distal articulable section includes a plurality of slots, and wherein the plurality of slots extend through less than an entire wall thickness of the distal articulable section.

\* \* \* \* \*